United States Patent [19]

Nohira et al.

[11] Patent Number: 5,066,826
[45] Date of Patent: Nov. 19, 1991

[54] PROCESS FOR RACEMIZATION OF OPTICALLY ACTIVE 4-PHENYLBUTANOIC ACID ESTERS

[75] Inventors: Hiroyuki Nohira, Urawa; Takashi Onishi; Kazuo Yamamoto, both of Kurashiki; Noriaki Kumagai, Kamisu, all of Japan

[73] Assignee: Kuraray Company, Ltd., Kurashiki, Japan

[21] Appl. No.: 588,545

[22] Filed: Sep. 26, 1990

[30] Foreign Application Priority Data

Oct. 6, 1989 [JP] Japan ................................. 1-262516

[51] Int. Cl.$^5$ ............................................. C07C 69/76
[52] U.S. Cl. ..................................................... 560/60
[58] Field of Search .......................................... 560/60

[56] References Cited

U.S. PATENT DOCUMENTS 4,837,354  6/1989  Flynn et al. .

FOREIGN PATENT DOCUMENTS 251058  1/1988  European Pat. Off. .
325971  8/1989  European Pat. Off. .
329156  8/1989  European Pat. Off. .
216954  8/1989  Japan .
247100  10/1989 Japan .
281098  11/1989 Japan .

Primary Examiner—Paul J. Killos
Attorney, Agent, or Firm—Oblon, Spivak, McClelland, Maier & Neustadt

[57] ABSTRACT

A process for the racemization of optically active 4-phenylbutanoic acid esters which comprises treating optically active 4-phenylbutanoic acid esters of the general formula (1)

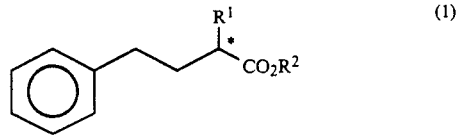

wherein $R^1$ represents a hydroxy group, a hydroxy group protected by vinyl ester, or a lower acyloxy group and $R^2$ represents a lower alkyl group with a base selected from the group consisting of alkali metal alcoholates, alkali metal hydrides, and alkali metal amides is provided.

6 Claims, No Drawings

PROCESS FOR RACEMIZATION OF OPTICALLY ACTIVE 4-PHENYLBUTANOIC ACID ESTERS

BACKGROUND OF THE INVENTION

1. Field of the Invention

This invention relates to a process for the racemization of optically active 4-phenylbutanoic acid esters of the general formula (1)

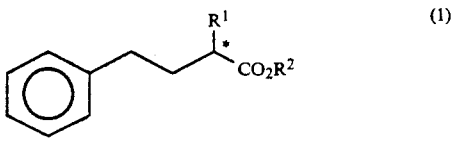

wherein $R^1$ represents a hydroxy group, a hydroxy group protected by vinyl ether, or a lower acyloxy group and $R^2$ represents a lower alkyl group.

Optically active 2-hydroxy-4-phenylbutanoic acid esters or derivatives thereof included in the aforementioned general formula (1) are useful as a starting substance for the synthesis of pharmaceuticals like angiotensin converting enzyme-inhibiting pharmaceuticals, such as Cilazapril, Quinapril, Enalapril, Indolapril, Ramipril, and Lisinopril.

2. Description of the Prior Art

A process for the racemization of optically active 4-phenylbutanoic acid esters in which 2-position is replaced by a hydroxy group, a hydroxy group protected by vinyl ether, or a lower acyloxy group has not been reported until today.

When optically inactive ($\pm$)-2-hydroxy-4-phenylbutanoic acid esters which can be synthesized by a following method are used as a starting substance for the preparation of aforementioned pharmaceuticals, the racemate must be optically resolved to separate into one conformation such as R($-$)-2-hydroxy-4-phenylbutanoic acid esters concerning the conformation of hydroxy group at 2-position.

Heretofore, the following two methods have been reported concerning optically resolving ($\pm$)-2-hydroxy-4-phenylbutanoic acid or esters thereof into its optically active forms respectively. One method is treating ($\pm$)-2-hydroxy-4-phenylbutanoic acid with an optically active menthol to form its menthyl esters, repeating recrystallization from petroleum ether to obtain an optically active menthyl ester (refer to "Optical Resolution Procedures for Chemical Compounds" pp 476 (1986) published by OPTICAL RESOLUTION INFORMATION CENTER, Manhattan Colledge, Riverdale, N.Y.); and the other method is treating ($\pm$)-2-hydroxy-4-phenylbutanoic acid with an optically active 1-(p-tolyl)ethylene amine or an optically active N-(2-hydroxy)ethyl-α-methylbenzyl amine as a resolving agent (refer to EP 0329156).

However, since a method for the racemization of optically active 2-hydroxy-4-phenylbutanoic acid and optically active 2-hydroxy-4-phenylbutanoic acid esters have not been reported heretofore, the useless optically active compound in the other form, recovered at the optical resolution of ($\pm$)-2-hydroxy-4-phenylbutanoic acid esters, has not been effectively utilized.

Accordingly, the object of the present invention is to provide a process for racemizing optically active 4-phenylbutanoic acid esters effectively and easily.

SUMMARY OF THE INVENTION

According to the present invention, the aforementioned object has been accomplished by a process treating an optically active 4-phenylbutanoic acid esters as shown in the following general formula (1)

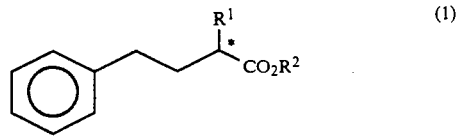

wherein $R^1$ represents a hydroxy group, a hydroxy group protected by vinyl ether, or a lower acyloxy group and $R^2$ represents a lower alkyl group with a base selected from the group consisting of alkali metal alcoholates, alkali metal hydrides, and alkali metal amides.

That is, the fact that little or no racemization reaction of optically active 2-hydroxy-4-phenylbutanoic acid can be carried out, but optically active 2-hydroxy-4-phenylbutanoic acid esters prepared from optically active 2-hydroxy-4-phenylbutanoic acid can readily be racemized by treating with a particular base as described above, was discovered and the present invention was completed.

DESCRIPTION OF THE PREFERRED EMBODIMENT $R^1$ and $R^2$ in the above general formula will be described in detail. Examples of $R^1$ include a hydroxy group; a so-called hydroxy group protected by vinyl ether such as a (tetrahydrofuran-2-yl)oxy group, a (tetrahydropyran-2-yl)oxy group, a (3-methyltetrahydropyran-2-yl)oxy group, a (1-ethoxy)ethoxy group, a (1-propoxy)ethoxy group, and a (1-butoxy)ethoxy group; and a lower acyloxy group such as a formyloxy group, an acetoxy group, a propionyloxy group, a butylyloxy group, an i-butylyloxy group, a valeryloxy group, and an i-valeryloxy group.

Optically active 2-hydroxy-4-phenylbutanoic acid esters having a hydroxy group as $R^1$ are particularly useful for a starting material for the synthesis of pharmaceuticals like angiotensin converting enzyme-inhibiting pharmaceuticals.

Also examples of $R^2$ include a lower alkyl group usually having 1–5 carbon atoms, such as a methyl group, an ethyl group, a propyl group, an i-propyl group, a butyl group, a s-butyl group, a t-butyl group, a pentyl group, and a neopentyl group.

Examples of optically active 4-phenylbutanoic acid esters as shown in the general formula (1) include S(+)-2-hydroxy-4-phenylbutanoic acid methyl ester, S(+)-2-hydroxy-4-phenylbutanoic acid ethyl ester, S(+)-2-hydroxy-4-phenylbutanoic acid propyl ester, S(+)-2-hydroxy-4-phenylbutanoic acid i-propyl ester, S(+)-2-hydroxy-4-phenylbutanoic acid butyl ester, S(+)-2-acetoxy-4-phenylbutanoic acid ethyl ester, S(+)-2-(tetrahydropyran-2-yl)oxy-4-phenylbutanoic acid ethyl ester and S(+)-2-(1-ethoxy)ethoxy-4-phenylbutanoic acid ethyl ester; and their optical antipodes, R($-$)-4-phenylbutanoic acid esters.

A process for preparing optically active 4-phenylbutanoic acid esters used as a starting material according to the present invention is illustrated in the followings.

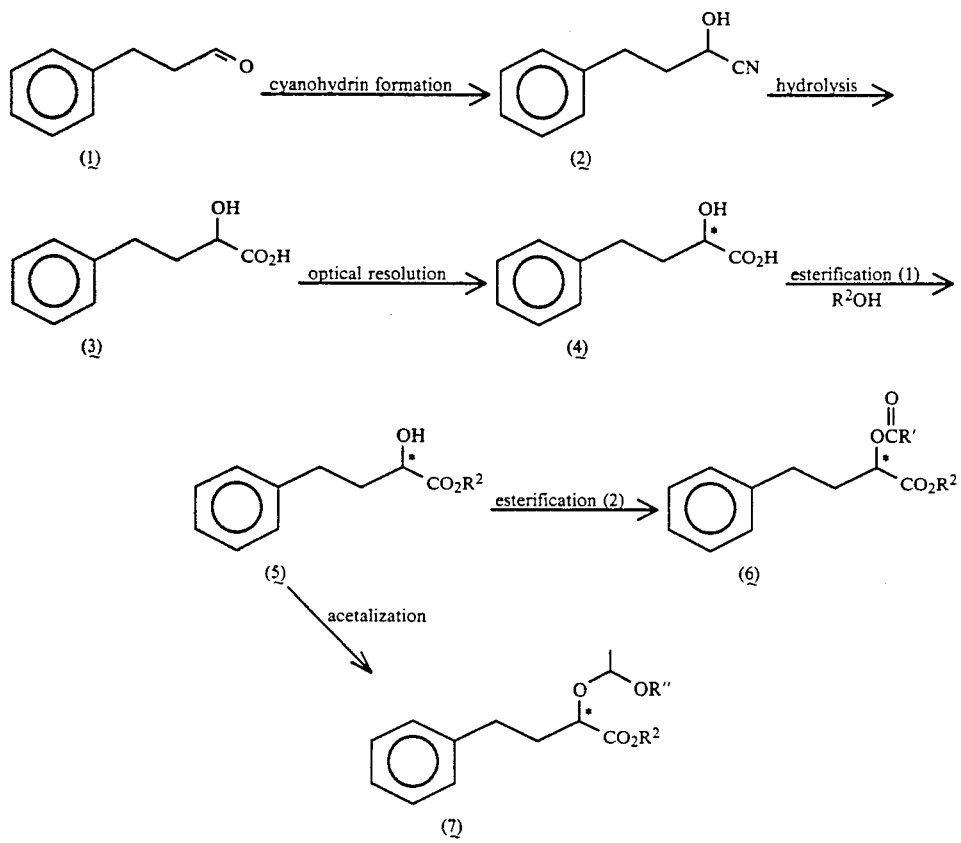

1) Cyanohydrin Formation 3-phenylpropanol (1) and hydrocyanic acid are reacted with a 10% aqueous sodium acetate solution as a catalyst, at a temperature of 20° to 25° C. for 30 min. to result in cyanohydrin (2).

2) Hydrolysis

Cyanohydrin (2) and concentrated hydrochloric acid are reacted at an inner temperature of 70° to 120° C. for 3 to 5 hours to result in (±)-2-hydroxy-4-phenylbutanoic acid (3).

3) Optical Resolution (Refer to EP 0329156)

(±)-2-hydroxy-4-phenylbutanoic acid (3) is treated with optically active 1-(p-tolyl)ethyl amine or optically active N-(2-hydroxy)ethyl-α-methylbenzyl amine with an amount of 0.4 to 1 equivalent to form corresponding diastereomeric salt.

Thereafter, the diastereomeric salt is separated into corresponding optically active R(−)- or S(+)-2-hydroxy-4-phenylbutanoic acid (4) by utilization of the difference of solubilities thereof to the solvent.

4) Esterification (1)

Optically active 2-hydroxy-4-phenylbutanoic acid (4) and a lower alcohol are reacted with an acidic catalyst, to result in optically active 2-hydroxy-4-phenylbutanoic acid ester (5). Examples of lower alcohol used in the reaction include methyl alcohol, ethyl alcohol, propyl alcohol, i-propyl alcohol, butyl alcohol, i-butyl alcohol, s-butyl alcohol, amyl alcohol and the like.

Examples of catalyst used for esterification reaction include mineral acids such as sulfuric acid, phosphoric acid etc. Among them, sulfuric acid is particularly preferable.

Preferable amount of catalyst used for the reaction is equivalent or less, more preferably 3 to 10 mole percent based on optically active 2-hydroxy-4-phenylbutanoic acid.

Preferable reaction temperature for the reaction, depending on the kind and amount of catalyst and those of lower alcohol, is usually in the range of 50° to 150° C.

The amount of lower alcohol used for the reaction based on optically active 2-hydroxy-4-phenylbutanoic acid is larger the better for advancing the esterification reaction smoothly, however, practically used amounts is preferably 1 to 5 mole equivalents to the acid.

Optically active 2-hydroxy-4-phenylbutanoic acid ester (5) can be isolated by pouring the reaction mixture into water and extracting it with solvent, followed by removal of solvent.

5) Esterification (2)

Optically active 2-hydroxy-4-phenylbutanoic acid ester (5) and an acid anhydride are reacted with dimethylaminopyridine as a catalyst at a room temperature to result in optically active 2-hydroxy-4-phenylbutanoic acid ester (6).

6) Acetalization

Optically active 2-hydroxy-4-phenylbutanoic acid ester (6) and vinyl ether are reacted with p-toluenesulfonic acid pyridine salt as a catalyst in methylene chloride solvent at a room temperature to result in optically active 2-(1-alkoxy)ethoxy-4-phenylbutanoic acid ester (7).

Then the racemization conditions according to the present invention are illustrated in the followings.

Racemization of optically active 4-phenylbutanoic acid ester derivatives of the general formula (1) is carried out in the presence of a base.

Examples of base pratically used in the invention include alkali metal alcohorates such as sodium methylate, sodium ethylate, potassium methylate, potassium ethylate and sodium t-butylate; alkali metal hydrides such as sodium hydride and potassium hydride; and alkali metal amides such as sodium amide, potassium amide and lithium amide. Among them, preferable bases are alkali metal alcoholates and alkali metal hydrides.

The amount of base used for racemization depends on the temperature and period of racemization reaction but usually 0.5 mole percent or more is used based on optically active 4-phenylbutanoic acid ester as shown in the general formula (1). Preferred amount of base is in the range of 1 to 10 mole percent from a reactivity and economic view.

The presence of water in the reaction system reduces its reactivity because of the reaction of base with water, therefore contamination of water must be avoided with sufficient care.

Racemization reaction can be carried out without any solvent. However, organic solvents inactive to base such as hydrocarbons like benzene, toluene, xylene, p-cymene, octane, decane, cyclohexane, etc.; ethers like butyl ether, i-butyl ether, anisol, etc. and dimethyl sulfoxide, hexamethylphosphoryl triamide, etc. can be used as a racemization solvent.

The amount of solvent used for racemization reaction is practically 1 to 10 equivalents based on substrate from an economical view.

Racemization reaction can be carried out at 50° C. or more, preferably in the range of 70° to 150° C.

The period for racemization required depends on the temperature and kind of base used. For example, the racemization period is about 1 hour when sodium hydride is used as a base in an amount of 2.5 mole percent based on substrate, under reflux of toluene.

The post-treatment of reaction mixture of racemization is as follows. After the reaction mixture is poured into a large amount of water or aqueous hydrochloric acid and extracted by the solvent used for racemization or i-propyl ether, the extracted solution is washed with water, followed by the removal of the solvent. The obtained ($\pm$)-4-phenylbutanoic acid ester is purified by distillation. Also ($\pm$)-4-phenylbutanoic acid esters can be converted to ($\pm$)-2-hydroxy-4-phenylbutanoic acid with a conventional chemical method, followed by purification of recrystallization. Examples of conversion method are described as follows.

(1) The Conversion of 2-Hydroxy-4-phenylbutanoic Acid Ester or 2-Acyloxy-4-phenylbutanoic Acid Ester to 2-Hydroxy-4-phenylbutanoic Acid After a 2-hydroxy-4-phenylbutanoic acid ester or a 2-acyloxy-4-phenylbutanoic acid ester and sodium hydroxide (5–10 mole times) are refluxed in ethanol solvent for 3 hours, ethanol is removed, followed by acidification of the system with aqueous hydrochloric acid to obtain 2-hydroxy-4-phenylbutanoic acid, which can be highly purified by recrystallization from aqueous solution.

(2) The Conversion of 2-(1-Alkoxy)ethoxy-4-phenylbutanoic Acid Ester to 2-Hydroxy-4-phenylbutanoic Acid In a hydrated tetrahydrofuran solvent, 2-(1-alkoxy)ethoxy-4-phenylbutanoic ester is treated with diluted hydrochloric acid at a room temperature for 3 hours, which causes a so-called deprotection reaction to result in 2-hydroxy-4-phenylbutanoic acid. Further, the substance can be converted to 2-hydroxy-4-phenylbutanoic acid by the same procedure (1) as described above.

The thus obtained ($\pm$)-2-hydroxy-4-phenylbutanoic acid can be subjected to optical resolution as described in procedure 3) to obtain the objective optically active 2-hydroxy-4-phenylbutanoic acid on one side. Also the useless optical antipode on the other side is esterified by aforementioned procedure 4), followed by racemization to convert into ($\pm$)-2-hydroxy-4-phenylbutanoic acid. The objective optically active body alone can be produced by repeating these procedures.

The present invention will be more particularly described by the following examples, which should not be construed as limiting the present invention.

EXAMPLE 1

In a 300 ml flask, 50 g of S(+)-2-hydroxy-4-phenylbutanoic acid ethyl ester, 0.24 g of sodium hydride (purity 60%), and 150 ml of dehydrated toluene were placed and heated under reflux for 1 hour. The reaction mixture was cooled to room temperature and was poured into 200 ml of 1% aqueous hydrochloric acid to stop the reaction, followed by separation of upper toluene layer. Further the lower layer was washed with 100 ml of toluene, and the extracted toluene was added to the formerly separated toluene, followed by washing with 200 ml of water in two times. Toluene was removed under reduced pressure to obtain 50.8 g of light yellow oily substance.

This oily substance was revealed to be S(+)-2-hydroxy-4-phenylbutanoic acid ethyl ester and R(−)-2-hydroxy-4-phenylbutanoic acid ethyl ester at an area ratio of 49.5:50.5 by liquid chromatographic analysis under the following conditions.

Liquid chromatographic analysis conditions:
Column; Chiralcel OD, 4.6×250 mm
Eluent; hexane/i-propanol (volume ratio; 9/1)
Flow rate; 0.5 ml/min.
Detector; UV (254 nm)

Also the oily substance was found to contain total 43.6 g of S(+)-2-hydroxy-4-phenylbutanoic acid ethyl ester and R(−)-2-hydroxy-4-phenylbutanoic acid ethyl ester by quantitative gas chromatographic analysis under the following conditions:

Gas chromatographic analysis conditions:
Column; Silicon OV-17, 2 m
Column temperature; 150° C.
Injection temperature; 230° C.

EXAMPLE 2–4

The same conditions of Example 1 were repeated except that various basic compounds were used instead of sodium hydride for racemizing S(+)-2-hydroxy-4-phenylbutanoic acid. The obtained results are shown in Table 1.

TABLE 1

| Example No. | Base (Amount based on substrate) | Area ratio of[1] S(+)/R(−) |
|---|---|---|
| 2 | Potassium hydride (2.5 mole %) | 49.9/50.1 |
| 3 | Sodium amide (5 mole %) | 49.5/50.5 |
| 4[2] | Potassium methylate (3 mole %) | 50.6/49.4 |

[1] S(+): S(+)-2-hydroxy-4-phenylbutanoic acid ethyl ester
R(−): R(−)-2-hydroxy-4-phenylbutanoic acid ethyl ester
Area ratio by liquid chromatographic analysis
[2] Xylene was used as a solvent instead of toluene.

EXAMPLE 5-11

The same conditions of Example 1 were repeated except that various solvents were used instead of toluene for racemizing S(+)-2-hydroxy-4-phenylbutanoic acid ethyl ester. The obtained results are shown in Table 2.

TABLE 2

| Example No. | Solvent | Area ratio[3] S(+)/R(−) |
|---|---|---|
| 5 | Butyl ether | 51.0/49.0 |
| 6 | Cyclohexane | 50.1/49.9 |
| 7 | Octane | 50.7/49.3 |
| 8[1] | — | 49.6/50.4 |
| 9 | p-Cymene | 49.9/50.1 |
| 10[2] | Dimethyl sulfoxide | 49.8/50.2 |
| 11[2] | Hexamethylphosphoryl triamide | 50.0/50.0 |

[1] No solvent: Temperature condition; 120° C.
[2] Temperature condition: Inner temperature; 80° to 90° C.
[3] S(+): S(+)-2-hydroxy-4-phenylbutanoic acid ethyl ester
R(−): R(−)-2-hydroxy-4-phenylbutanoic acid ethyl ester
Area ratio by liquid chromatographic analysis

EXAMPLES 12-14

The same conditions of Example 1 were repeated except that various optically active 2-hydroxy-4-phenylbutanoic acid esters were used instead of S(+)-2-hydroxy-4-phenylbutanoic acid ethyl ester for racemization.

The obtained results are shown in Table 3. The analysis of reaction products were carried out under the same conditions of Example 1.

TABLE 3

| Example No. | Optically active 2-hydroxy-4-phenylbutanoic acid ester[1] | Area ratio[2] S(+)/R(−) |
|---|---|---|
| 12 | S(+)-2-hydroxy-4-phenylbutanoic acid methyl ester | 49.9/50.1 |
| 13 | S(+)-2-hydroxy-4-phenylbutanoic acid i-propyl ester | 50.5/49.5 |
| 14 | R(−)-2-hydroxy-4-phenylbutanoic acid ethyl ester | 49.9/50.1 |

[1] Optical purity of raw material is 99% or more.
[2] S(+): S(+)-2-hydroxy-4-phenylbutanoic acid ester
R(−): R(−)-2-hydroxy-4-phenylbutanoic acid ester
Area ratio by liquid chromatographic analysis

EXAMPLE 15

<Preparation of S(+)-2-hydroxy-4-phenylbutanoic acid ethyl ester>

To a 1000 ml flask, 88.2 g of S(+)-2-hydroxy-4-phenylbutanoic acid, 352 g of ethyl alcohol, 200 g of hexane and 2 g of concentrated sulfuric acid were placed, and water generated by reaction was removed by azeotropic distillation. The reaction was completed when the separation of water was ceased.

Thereafter, to the reaction mixture was added 400 ml of water and 400 ml of i-propyl ether, followed by separation of the organic layer. After the separated organic layer was washed with 1% aqueous sodium carbonate solution, i-propyl ether was removed under reduced pressure to obtain 110.2 g of light yellow oily substance.

The oily substance was revealed to contain 102.0 g of 2-hydroxy-4-phenylbutanoic acid ethyl ester by gas chromatographic analysis. Also, the oily substance was revealed to contain S(+)-2-hydroxy-4-phenylbutanoic acid ethyl ester and R(−)-2-hydroxy-4-phenylbutanoic acid ethyl ester at a ratio of 99.5/0.5 by liquid chromatographic analysis, which showed that no racemization was occurred under the ethyl esterification conditions. The gas chromatographic and liquid chromatographic conditions were the same as Example 1.

<Racemization>

In a 2000 ml flask, 100 g of S(+)-2-hydroxy-4-phenylbutanoic acid ethyl ester, 0.48 g sodium hydride (purity 60%, oily) and 300 ml of toluene were placed and reacted under reflux for 1 hour.

<Hydrolysis>

After toluene was distilled off under reduced pressure from the reaction mixture as described above, 1000 ml of ethyl alcohol and 288 g of 20% aqueous sodium hydroxide solution were added and reacted under reflux for 2.5 hours.

After the completion of reaction, ethyl alcohol was distilled off under reduced pressure, thereafter 300 g of water was added, followed by adjustment of pH of the system in a range of 1-2 with the addition of concentrated hydrochloric acid. Thereafter the reaction mixture was kept standing for 5 hours at 5° to 10° C., the reaction mixture was filtered and the filtrate was dried to obtain 73.0 g of white crystals.

The NMR spectrum of the white crystals was revealed to be the same as that of 2-hydroxy-4-phenylbutanoic acid. Also these crystals were found to contain S(+)-2-hydroxy-4-phenylbutanoic acid and R(−)-2-hydroxy-4-phenylbutanoic acid in a ratio of 50.1 to 49.9 by liquid chromatographic analysis.

Liuquid chromatographic analysis conditions:
Column; CHIRALPAK WH, 4.6×250 mm
Eluent; H$_2$O, 0.25 mM CuSO$_4$
Flow rate; 0.5 ml/min.
Detector; UV (254 nm)

EXAMPLE 16

<Acetalization>

In a 200 ml flask, 10.97 g of S(+)-2-hydroxy-4-phenylbutanoic acid ethyl ester, 20 ml of ethyl vinyl ether and 40 ml of methylene chloride were placed, to which was further added 0.1 g of p-toluene sulfonic acid pyridine salt.

The mixture was reacted at an inner temperature of 10° to 15° C. for 2 hours. After the completion of reaction, the reaction mixture was washed with 2% aqueous sodium carbonate solution, followed by removal of methylene chloride to obtain 14.75 g of light yellow crude 2-(1-ethoxy)ethoxy-4-phenylbutanoic acid ethyl ester. Further, a very small portion of the obtained compound was deprotected by acid to get 2-hydroxy-4-phenylbutanoic acid. The deprotected compound were analyzed by liquid chromatography under the same conditions of Example 1, which showed no racemization was occurred.

<Racemization>

The reaction product as obtained above was dissolved in 50 ml of toluene, to which 0.25 g of sodium hydride (purity 60%, oily) was further added. The mixture was reacted for 1 hour under reflux. The obtained reaction mixture was washed with 100 ml of water and from which toluene was distilled off under reduced pressure to get 14.30 go of yellow oily substance.

<Deprotection>

To the aforementioned oily substance was added 70 ml of tetrahydrofuran and 10 ml of 5% aqueous hydrochloric acid. The mixture was reacted at room temperature for 2 hours. After the completion of the reaction, 200 ml of water was added to the reaction mixture, followed by extraction with 200 ml of i-propyl ether to obtain 10.98 g of yellow oily substance.

The oily substance was revealed to contain 10.30 g of 2-hydroxy-4-phenylbutanoic acid ethyl ester by gas chromatographic analysis. Also, the oily substance was revealed to contain S(+)-2-hydroxy-4-phenylbutanoic acid ethyl ester and R(−)-2-hydroxy-4-phenylbutanoic acid ethyl ester in an area ratio of 50.0 to 50.0 by liquid chromatographic analysis under the same conditions as Example 1.

EXAMPLE 17

The same procedures as Example 16 (Acetalization, Racemization and Deprotection) were repeated except that instead of 10.97 g of S(+)-2-hydroxy-4-phenylbutanoic acid ethyl ester and 20 ml of ethyl vinyl ether, 10.97 g of R(−)-2-hydroxy-4-phenylbutanoic acid ethyl ester and 30 ml of 3,4-dihydro-2H-pyran were used, thereby obtaining 10.75 g of yellow oily substance.

The oily substance was revealed to contain 10.15 g of 2-hydroxy-4-phenylbutanoic acid ethyl ester by gas chromatographic analysis. Also the oily substance was revealed to contain S(+)-2-hydroxy-4-phenylbutanoic acid ethyl ester and R(−)-2-hydroxy-4-phenylbutanoic acid ethyl ester in an area ratio of 49.8 to 50.2 by liquid chromatographic analysis under the same conditions as Example 16.

EXAMPLE 18

<Acetylation>

In a 50 ml flask, 2.08 g of S(+)-2-hydroxy-4-phenylbutanoic acid ethyl ester, 3 g of acetic anhydride and 0.05 g of dimethylaminopyridine were placed, and the reaction was carried out at 40° to 50° C. for 5 hours. After the completion of the reaction, the reaction mixture was poured into 50 ml of 5% aqueous sodium carbonate solution, followed by extraction with 50 ml of i-propyl ether. The extracted solution was washed with 5 ml of 1% aqueous sodium carbonate solution, followed by removal of i-propyl ether under reduced pressure, to obtain 2.55 g of light yellow oily substance.

Further, a very small portion of this oily substance was hydrolyzed and analyzed under the same conditions as described in Example 15, which revealed that no racemization was occurred.

<Racemization>

The obtained oily substance was dissolved in 10 ml of toluene, to which further added 0.05 g of sodium hydride (purity 60%, oily). The mixture was reacted under reflux for 0.5 hour. After the completion of the reaction, toluene was distilled off under reduced pressure to obtain 2.50 g of yellow oil.

<Hydrolysis>

To the oily substance, 40 ml of ethanol and 10 g of 20% aqueous sodium hydroxide solution were added. The mixture was reacted under reflux. After the completion of reaction, ethanol was removed under reduced pressure, pH value of the system was adjusted to 1–2 by adding 10% aqueous hydrochloric acid.

The precipitated crystals were separated by filteration and dried to obtain 1.61 g of 2-hydroxy-4-phenylbutanoic acid. The obtained crystals were revealed to contain S(+)-2-hydroxy-4-phenylbutanoic acid and R(−)-2-hydroxy-4-phenylbutanoic acid in an area ratio of 50.4 to 49.6 by the same analytical conditions as Example 15.

Comparative Example 1

An example of preparing processes of optically active 2-hydroxy-4-phenylbutanoic acid esters which can be used as a starting material for the present invention is described as follows.

<Synthesis of 2-hydroxy-4-phenylbutyronitrile>

In a 300 ml flask, 134 g of 3-phenylpropanal and 1.4 g of 10% aqueous sodium acetate solution were placed, to which 27 g of hydrocyanic acid was added in dropwise maintaining the reaction temperature at 20° to 25° C., thereafter the reaction mixture was kept standing for 30 min.

Liquid chromatographic analysis conditions:
Column; Lichrosorb RP-18, 4.6×250 mm
Eluent; MeOH/H$_2$O in a ratio of 6/4, H$_3$PO$_4$ 2 mmol/liter
Flow rate; 0.5 ml/min.
Detector; UV (254 nm)

<Preparation of 2-hydroxy-4-phenylbutanoic acid>

In a 1000 ml flask, 135.6 g of concentrated hydrochloric acid was placed, to which the aforementioned reaction solution was added in dropwise keeping the inner temperature at 50° to 55° C. After the completion of addition in dropwise, the reaction was continued keeping the inner temperature at 90° C. for 3 hours, thereafter the reaction mixture was cooled to the inner temperature being 15° to 20° C. 2-Hydroxy-4-phenylbutanoic acid was precipitated in white crystals. The crystals were separated by filtration and dried to obtain 126 g of 2-hydroxy-4-phenylbutanoic acid. Liquid chromatographic analysis conditions were the same as that of 2-hydroxy-4-phenylbutyronitrile.

<Preparation of S(+)-2-hydroxy-4-phenylbutanoic acid>

To 350 g water, 126 g of 2-hydroxy-4-phenylbutanoic acid prepared as described above, 56.7 g of (−)-1-(p-tolyl)ethylamine and 11.2 g of sodium hydroxide were dissolved. After standing overnight for cooling, the precipitated crystals were separated by filtration to obtain 83.3 g of S(+)-2-hydroxy-4-phenylbutanoic acid (−)-1-(p-tolyl)ethylamine salt. To the thus obtained crystals were added 280 ml of 1N aqueous sodium hydroxide solution, followed by extraction with ether.

The ether layer was separated and dried with sodium sulfate anhydride. The solvent of the extract was distilled off under reduced pressure to obtain 44.1 g of S(+)-2-hydroxy-4-phenylbutanoic acid in white crystals. The crystals were revealed to contain S(+)-2-hydroxy-4-phenylbutanoic acid and R(−)-2-hydroxy-4-phenylbutanoic acid in a ratio of 99.5 to 0.5 by liquid chromatographic analysis. The liquid chromatographic analysis conditions were the same as Example 15.

Comparative Examples 2-3

According to the following conditions, racemization reactions of S(+)-2-hydroxy-4-phenylbutanoic acid were carried out, but little or no racemization was occurred.

| Comparative Example No. | Base (Amount based on substrate, mole times) | Solvent | Conditions | S/R[1)2)] |
| --- | --- | --- | --- | --- |
| 2 | Sodium methylate (10) | Methanol | Under reflux 5.5 hr. | 95/5 |
| 3 | Sodium hydride (2.5) | Toluene | Under reflux 3 hr. | 95/5 |

[1)]S/R: Ratio of S(+)-2-hydroxy-4-phenylbutanoic acid to R(−)-2-hydroxy-4-phenylbutanoic acid. Starting ratio: S/R = 95/5.
[2)]Liquid chromatographic analysis conditions were the same as described in Example 15.

What is claimed is:

1. A process for the racemization of optically active 4-phenylbutanoic acid esters which comprises treating optically active 4-phenylbutanoic acid esters of the general formula (1)

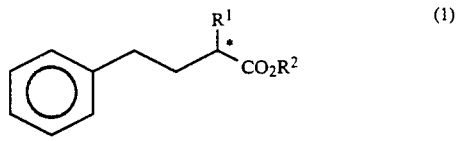

wherein $R^1$ represents a hydroxy group, a hydroxy group protected by vinyl ether, or a lower acyloxy group and $R^2$ represents a lower alkyl group with a base selected from the group consisting of alkali metal alcoholates, alkali metal hydrides, and alkali metal amides.

2. A process of claim 1 wherein said optically active 4-phenylbutanoic acid esters are S(+)-2-hydroxy-4-phenylbutanoic acid esters.

3. A process of claim 1 wherein the amount of base used is 0.5 mole percent or more based on optically active 4-phenylbutanoic acid ester.

4. A process of claim 3 wherein the amount of base used is 1-10 mole percent based on optically active 4-phenylbutanoic acid ester.

5. A process of claim 1 wherein the reaction is carried out at 50° C. or more.

6. A process of claim 5 wherein the reaction is carried out at a temperature in the range of 70° to 150° C.

* * * * *